US011257603B2

(12) United States Patent
Maciocco et al.

(10) Patent No.: US 11,257,603 B2
(45) Date of Patent: Feb. 22, 2022

(54) ACCELERATOR-DRIVEN NEUTRON ACTIVATOR FOR BRACHYTHERAPY

(71) Applicant: ADVANCED ACCELERATOR APPLICATIONS, Saint Genis Pouilly (FR)

(72) Inventors: Luca Maciocco, Crozet (FR); Stefano Buono, New York, NY (US)

(73) Assignee: ADVANCED ACCELERATOR APPLICATIONS, Saint Genis Pouilly (FR)

( * ) Notice: Subject to any disclaimer, the term of this patent is extended or adjusted under 35 U.S.C. 154(b) by 144 days.

(21) Appl. No.: 16/605,543

(22) PCT Filed: Apr. 24, 2018

(86) PCT No.: PCT/EP2018/060416
§ 371 (c)(1),
(2) Date: Oct. 16, 2019

(87) PCT Pub. No.: WO2018/197451
PCT Pub. Date: Nov. 1, 2018

(65) Prior Publication Data
US 2020/0126683 A1    Apr. 23, 2020

(30) Foreign Application Priority Data
Apr. 24, 2017  (EP) .................................. 17305461

(51) Int. Cl.
*G21G 1/06* (2006.01)
*A61N 5/10* (2006.01)
(Continued)

(52) U.S. Cl.
CPC .............. *G21G 1/06* (2013.01); *A61N 5/1001* (2013.01); *A61N 2005/1091* (2013.01);
(Continued)

(58) Field of Classification Search
CPC ............. G21G 1/06; G21G 2001/0094; G21K 1/06; H05H 3/06; A61N 5/1001; A61N 2005/1091
(Continued)

(56) References Cited

U.S. PATENT DOCUMENTS

| 3,325,371 A * | 6/1967 | Stanton | .................... G21C 1/00 |
| | | | 376/194 |
| 2010/0067640 A1* | 3/2010 | Willis | ...................... H05H 3/06 |
| | | | 376/194 |
| 2013/0142296 A1* | 6/2013 | Pieter | ....................... G21G 1/06 |
| | | | 376/190 |

FOREIGN PATENT DOCUMENTS

WO         98/59347       12/1998
WO      2008/017944       2/2008
(Continued)

*Primary Examiner* — Peter M Poon
*Assistant Examiner* — Daniel Wasil
(74) *Attorney, Agent, or Firm* — Clark & Brody LP

(57) ABSTRACT

A neutron activator for neutron activation of a material, the neutron activator being configured to produce neutrons from an interaction with a proton beam (7), the neutron activator comprising:
 a neutron source comprising a metallic target (1), and
 a Beryllium first reflector-moderator (4) peripheral to the neutron source and comprising a neutron activation area (10) configured to accommodate the neutron source and the material to be activated, the neutron activation area (10) of the first reflector-moderator (4) comprising a bore configured to accommodate the neutron source.

26 Claims, 5 Drawing Sheets

(51) Int. Cl.
*G21G 1/00* (2006.01)
*G21K 1/06* (2006.01)
*H05H 3/06* (2006.01)

(52) U.S. Cl.
CPC ....... *G21G 2001/0094* (2013.01); *G21K 1/06* (2013.01); *H05H 3/06* (2013.01)

(58) Field of Classification Search
USPC .................................................. 376/184, 194
See application file for complete search history.

(56) References Cited

FOREIGN PATENT DOCUMENTS

WO     2016/022848     2/2016
WO     2016/037656     3/2016

\* cited by examiner

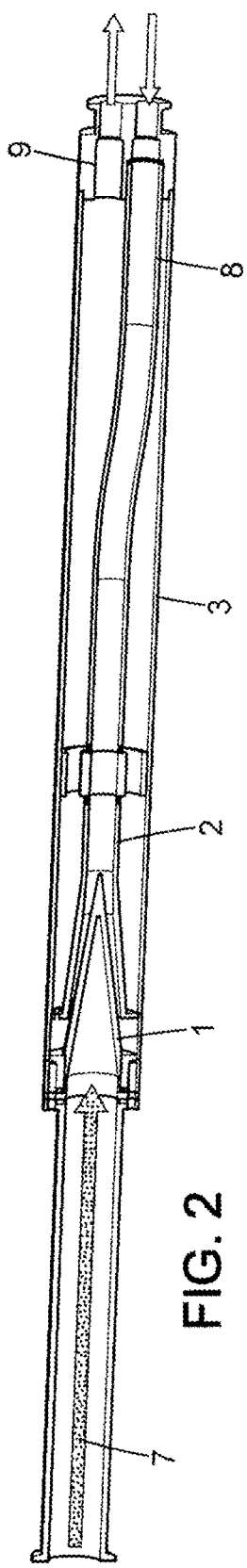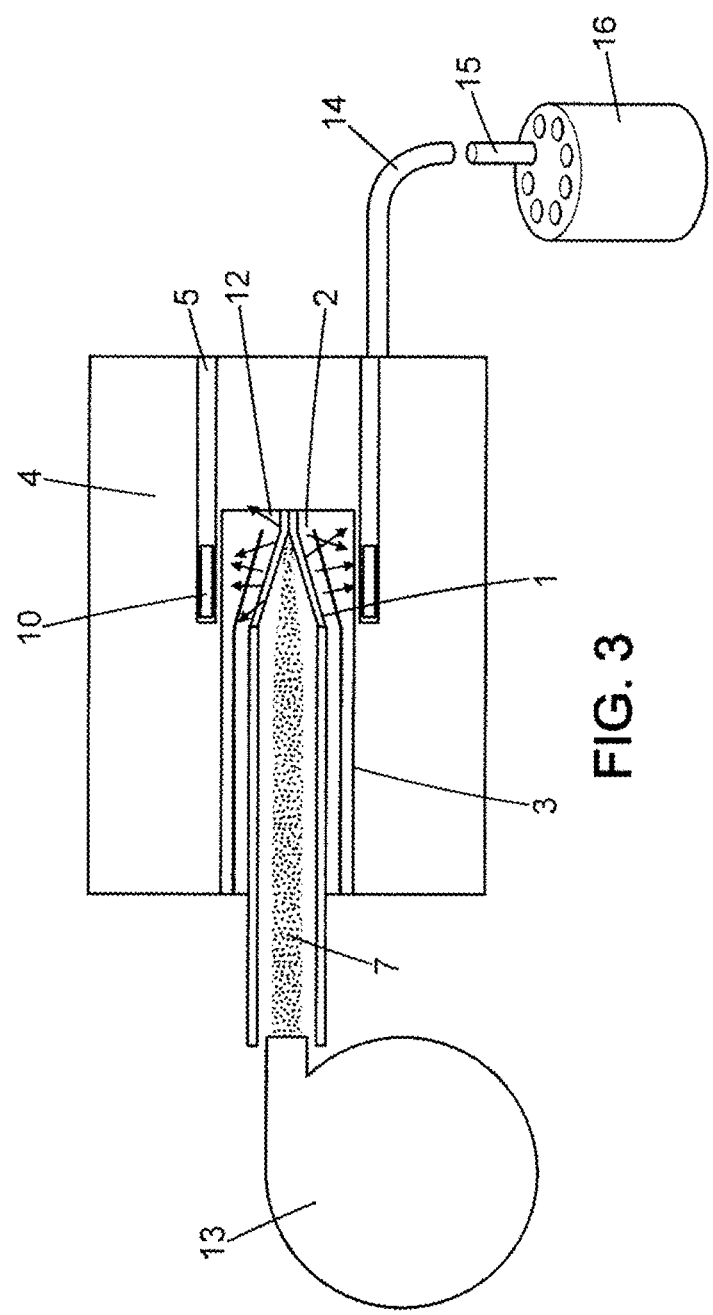

ACCELERATOR-DRIVEN NEUTRON ACTIVATOR FOR BRACHYTHERAPY

TECHNICAL FIELD

The field of the invention is that of activation of doses of injectable suspensions of particles through the production of a suitable neutron field.

The invention particularly relates to a neutron activator for production of radioisotopes of interest, which operating principle is based on the interaction of a proton beam with a solid target, which generates neutrons that are then moderated/reflected in a solid assembly to obtain a favourable neutron spectrum for the (n, γ) reactions in the isotopes of interest (for example $^{165}$Ho, and $^{176}$Lu).

BACKGROUND ART

Treatment of cancer tumours is based on three main therapeutic classes (frequently combined for increasing the chances of recovery): surgery, chemotherapy and external radiotherapy.

Brachytherapy or "in situ" radiotherapy is often recommended in addition to surgery or chemotherapy (as in breast or cervical tumors), or in alternative, constituting then the exclusive first-line treatment (as in prostate cancer in US, treatment of hepatocarcinomas, or other hepatic tumors).

Rapidly dividing cells are particularly sensitive to damage by radiation. For this reason, some cancerous growths can be controlled or eliminated by administering or planting a small radiation source, usually a gamma or beta emitter, in the target area.

The main advantage of brachytherapy procedures it that they give less overall radiation to the body, minimising the exposure of healthy tissues, are more localized to the target tumor and are cost-effective.

β'-emitting radioisotopes can be produced through neutron irradiation of the corresponding stable isotopes.

Currently such isotopes are produced only in research nuclear reactors, but the main disadvantages rely on the low availability of reactors in Europe for medical use, combined with tight schedule and ageing problems.

Consequently, a need still exists for alternative methods for the efficient production of neutron-activated radioisotopes using cyclotrons for medical applications.

One of the objects of the present disclosure is to propose an alternative to the production of radioisotopes for medical use, in nuclear reactors.

Another object is to improve the efficiency of the method of production of radioisotopes for medical use.

Another object of the invention is to provide a device and a method for neutron activation of a material, for producing radioisotopes.

WO 98/59347 discloses that a material exposed to a neutron flux by distributing it in a neutron-diffusing medium surrounding a neutron source can be used to produce useful radio-isotopes, in particular for medical applications, from the transmutation of readily-available isotopes included in the exposed material. The neutron source consists of a beryllium or lithium target bombarded with a charged particle beam.

A major drawback of this method is that the dimensions of the activator are very big in order to contain the neutrons within the system during their elastic-scattering path in the material. This also results in a relevant dilution of the neutron flux, in particular at lower energies (so after several scattering interactions).

WO 2016/037656 discloses a method and an activator that enhances captures in the resonance region. The strength of the flux of neutrons is optimized by reflectors and/or moderators.

With respect to WO 98/59347, it proposes some general approaches aiming at reducing the activator size while exploiting the neutron-elastic-scattering properties of lead, and therefore the Adiabatic Resonance Crossing principle in the activation area. This approach has been numerically and experimentally analysed in 2005-2009 by the inventors with the experimental validation of an activator with a lead core and a graphite reflector. The results of such research led to the conclusion that the most efficient approach to activate the considered isotopes was not to use the peculiar properties of lead (transparency and elastic scattering) but focusing on an efficient moderation-reflection, which provides the solution of the present invention. Furthermore, in preferred embodiment of the invention, the optimal position of the samples is as close as possible to the proton target rather than in specific positions in the so-called Diffuser.

WO 2016/022848 discloses neutron source comprising a spherical metallic target and a spherical reflector-moderator surrounding the target, the target and the reflector-moderator being immersed in a medium containing the material to activate.

With the neutron source of WO 2016/022848, the material is randomly activated which increases the time for activating the material and prevents large amounts of activated material to be obtained. In addition, recovery of the activated material is complex and not adapted to radioisotopes suitable for nuclear medicine therapy with short half-lives as the case for the present invention. The neutron activator configuration, especially the reflector position of WO 2016/022848 will not allow favorable activation yield for radioisotopes other than Mo-99, as produced by the following neutron capture reaction Mo-98(n,γ)Mo-99. The size of the reflector and potential based material (like heavy-water presented in the description) implies industrial and maintenance complexity as well as preventing from a compact process. Finally the cooling process involved cryogenic method that as opposite to the use of water cooling will led to much more complex usage and maintenance.

Another object of the disclosure is therefore to provide an improved system compared to the activator disclosed in WO 98/59347, WO 2016/037656 and WO 2016/022848.

SUMMARY

These and other objects are achieved by the presently disclosed neutron activator for neutron activation of a material, the neutron activator being configured to produce neutrons from an interaction with a proton beam emitted along a beam axis, the proton beam having an energy comprised between 16 MeV and 100 MeV, preferably 30 MeV and 70 MeV and a beam intensity up to 1 mA, preferably up to 350 μA for 70 MeV and up to 1 mA for 30 MeV, the neutron activator comprising:
- a neutron source comprising a metallic target presenting a longitudinal axis intended to be arranged parallel, and especially coaxial, to the beam axis, and
- a Beryllium reflector-moderator peripheral to the neutron source and comprising a neutron activation area configured to accommodate the neutron source and the material to be activated, the neutron activation area of the Beryllium reflector-moderator comprising a bore extending along a bore axis and configured to accommodate the neutron source so that the bore axis and the longitudinal axis are coaxial.

The neutron activation area of the Beryllium reflector-moderator may further include at least one activation channel extending along a channel axis parallel to the bore axis at the vicinity of the bore, the activation channel being configured to load the material to be activated.

The neutron activation area may comprise a plurality of activation channels distributed, especially equally distributed, around the bore.

The metallic target may have a hollow conical shape, the longitudinal axis of said conical target being aligned with the proton beam and the neutron activator further comprises a cooling area in direct contact with the outer surface of the target for receiving a flow of fluid for cooling the target during neutron generation. Said cooling fluid may be a liquid, for example water. Provisions as to the shape of the metallic target could be complementary or alternative to the aforementioned provisions regarding the Beryllium reflector-moderator. That is, the shape of the metallic target could be provided independently of the provisions regarding the Beryllium reflector-moderator.

In such embodiment, the aperture of the conical target and the thickness of its lateral walls may be optimized so that
(i) part of the protons received from the proton beam have sufficient energy to release the fraction of the thermal energy corresponding to the Bragg peak outside the target,
(ii) the power density inside the target is reduced to at least 50% as compared to the power density in a target where all the protons received from the proton beam release their thermal energy inside the target, and
(iii) the number of generated neutrons in the target is at least 70% equal to the number of generated neutrons in a target having a thickness where all the protons received from the proton beam release their thermal energy inside the target.

Alternatively, the aperture of the conical target and the thickness of its lateral walls may be optimized so that
(i) the protons received from the proton beam lose all their energy within the metallic target, and
(ii) the stresses generated by the temperature gradients in the target remain within the elastic limit of the metallic target, while still keeping the cooling liquid temperature below the boiling point.

Advantageously, the aperture of the hollow conical target is comprised between 20° and 45°.

The neutron activator may further comprise, housed in the reflector-moderator:
an inlet channel conveying the cooling fluid to a flow guide,
a flow guide delimiting the cooling area for guiding the cooling fluid along the outer surface of the target and obtain the desired velocity as a flow from the inlet channel to the outlet channel,
an outlet channel for removing the cooling fluid from the flow guide.

Preferably, the above-defined flow guide is at least partly conical so that said conical flow guide covers the outer surface of the conical target thereby delimiting a cooling area surrounding the outer surface of the target.

In specific embodiments which can be combined with any of the previous embodiments, the metallic target is made of Beryllium or Tantalum.

In a specific embodiment which can be combined with any of the previous embodiments, the Beryllium reflector-moderator is cylindrical along the bore axis.

Typically, the neutron activator may present an overall dimension that does not exceed the volume of a cube of 1 meter side, preferably 0.75 meter side, and for example 0.50 meter side.

The neutron activator may further comprise a second reflector-moderator embedding said Beryllium reflector-moderator.

The invention also relates to a neutron activation system for neutron activation of a material, comprising:
a generator configured to produce a proton beam along a beam axis, the proton beam having an energy comprised between 16 MeV and 100 MeV, preferably 30 MeV and 70 MeV and a beam intensity up to 1 mA, preferably up to 350 µA for 70 MeV and up to 1 mA for 30 MeV,
a neutron activator as defined previously arranged so that the longitudinal axis of the target is parallel, especially coaxial, to the beam axis.

When the neutron activation area of the Beryllium reflector-moderator includes at least one activation channel, the neutron activation system may further comprises a supplying device for loading the material to be activated, the supplying device being connected to the activation channel and configured to move samples of material to be activated along the activation channel.

The present invention also relates to the use of the neutron activator as previously described, for producing radioisotopes, preferably radiopharmaceuticals. For example, said radioisotope is a $\beta^-$ emitting radioisotope suitable for Nuclear Medicine applications, preferably $^{166}$Ho, $^{186}$Re, $^{188}$Re, $^{177}$Lu, $^{195}$Au, $^{90}$Y, $^{227}$Ra and $^{161}$Tb.

Another object of the present invention is a method for neutron activation of a material, said method comprising:
a) providing the material to be activated,
b) placing the material at the activation area of a neutron activator as defined previously,
c) generating a proton beam at an energy suitable for neutron activation of said material, thereby activating said material.

In a specific embodiment of the above-defined method using a neutron activator with a conical target as described above, the target is cooled by a flow of cooling liquid, preferably water, at a static pressure comprised between 1 and 20 Bar and reaching, near the target surface, speeds comprised between 8 and 15 m/s.

In another specific embodiment of the method, said material to be activated is contained within or in the form of a microparticle or nanoparticle, for example of Holmium-oxide micro/nanoparticles. Typically, the micro/nanoparticles are in a liquid suspension.

In a specific embodiment, said material is contained in a capsule, and said capsule is placed at the activation area by moving the capsule within an activation channel embedded in the reflector-moderator.

BRIEF DESCRIPTION OF THE DRAWINGS

The invention will be understood more clearly with the following detailed description of a preferred but non-limiting embodiment. This detailed description is given with reference to the attached drawings, in which:

FIG. 2 is a schematic illustration of a cylinder-shaped target assembly including the hollow conical target and its cooling system, FIG. 3 is a schematic illustration of the method for neutron activation using a neutron activator according to the present disclosure.

DETAILED DESCRIPTION

The present disclosure relates to a neutron activator for neutron activation of a material comprising:
- a neutron source comprising a metallic target suitable for receiving a proton beam of energy comprised between 16 and 100 MeV, preferably between 30 and 70 MeV, and capable of sustaining beam intensities up to 1 mA, preferably up to 350 µA for 70 MeV and up to 1 mA for 30 MeV and
- a Beryllium first reflector-moderator peripheral to the neutron source and comprising a neutron activation area,
- optionally, a second reflector-moderator embedding said Beryllium reflector-moderator.

The neutron activator according to the invention advantageously provides an optimized flux of neutrons having the energy of interest in the localized area around the samples to be activated, while remaining sufficiently compact for its use with small-medium sized cyclotrons.

It is therefore appropriate to perform a routine and industrial production of activated doses of radioisotopes, for use in pre-clinical and clinical studies, as well as for product commercialization.

Figure 1:
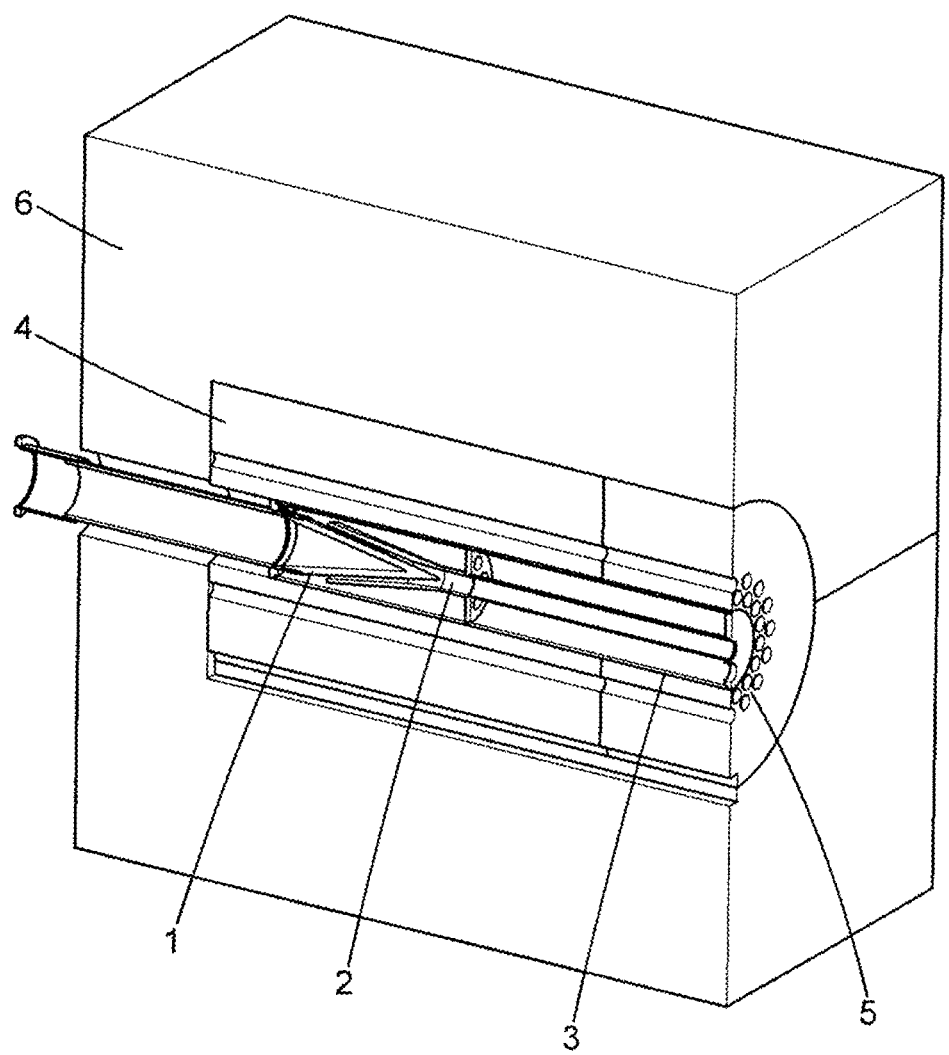
FIG. 1 is a schematic illustration of the neutron activator according to the present disclosure.

An embodiment of the neutron activator according to the present disclosure is illustrated at FIG. 1.

More specifically, a neutron activator of the present disclosure may comprise:
- a metallic hollow conical target as neutron source,
- a cooling system including a flow guide and a cooling container for guiding a cooling fluid along the outer surface of the conical target,
- a first Beryllium reflector-moderator surrounding the cooling container and hosting the activation channels disposed around the target,
- a second reflector-moderator embedding the first Beryllium reflector-moderator.

In particular, the neutron activator may comprise, housed in the reflector-moderator:
- a metallic hollow conical target as neutron source,
- a flow guide delimiting the cooling area, for guiding the cooling fluid along the outer surface of the target, as a flow from an inlet channel to an outlet channel,
- an inlet channel conveying the cooling fluid to the flow guide,
- an outlet channel for removing the cooling fluid from the flow guide.

An example of a cylinder-shaped target assembly including the hollow conical metallic target and its cooling system is provided in FIG. 2. In such specific embodiment, the target as neutron source is a hollow conical metallic target which longitudinal axis is aligned with the beam axis of the proton beam. The cooling system includes (i) a cooling container delimiting an inlet channel and an outlet channel for circulation of the cooling fluid, and (ii) a flow-guide delimiting the cooling area for guiding the cooling fluid along the outer surface of the hollow conical metallic target, as a flow from the inlet channel to the outlet channel.

The Metallic Target as Neutron Source

The neutron source is made of a metallic target presenting a longitudinal axis intended to be arranged parallel to the beam axis of the proton beam for receiving the proton beam which is advantageously generated by a cyclotron. In the represented embodiment, the longitudinal axis and the beam axis are coaxial, namely superposed. In other embodiments, the longitudinal axis and the beam axis could be parallel and spaced apart from each other.

Accordingly, the target body should be capable of sustaining proton beam of low energy and high intensity, for example, a proton beam energy comprised between 16 and 100 MeV, preferably between 30 and 70 MeV and beam intensities up to 1 mA, preferably up to 350 µA for 70 MeV and up to 1 mA for 30 MeV.

Embodiment with Conical Target Body

The target body preferably has a hollow conical shape. The conical shape of the target when aligned with the proton beam enables to optimize the yield of neutrons reaching the activation area surrounding the target. In particular, a conical shape of the target with a small aperture angle advantageously increases the interaction surface between the proton beam and the inner surface of the target, thereby lowering the power density in the target while increasing the surface for thermal cooling.

As used herein, the term "conical shape" is used with his broad meaning and refer to cones of circular or non-circular bases (for example the base could be of polygonal or elliptic or any other shape). In a preferred embodiment, the conical shape is a right circular cone.

As used herein, the team "hollow" conical shape means that the target is open at its base and essentially consists of the lateral walls of the cone.

The longitudinal axis of said hollow conical target is aligned with the proton beam generated by a cyclotron. Accordingly, the proton beam reaches the hollow conical target from the inner surface of the lateral walls of the conical target.

The neutron activator advantageously further comprises a cooling area in direct contact with the outer surface of the conical target for receiving a flow of fluid for cooling the target during neutron generation.

The final dimensions of the hollow conical metallic target and the cooling area will be adapted with the aim of optimizing the generation of neutrons.

In an embodiment of the neutron activator, the aperture of the conical target and the thickness of its lateral walls are preferably optimized so that part of the protons received from the proton beam have sufficient energy to release the fraction of the thermal energy corresponding to the Bragg peak outside the target in the cooling area, where this heat is easily removed by the cooling flow. This allows to significantly reduce the power density in the solid target, and so improve the target thermal conditions, without significantly reducing the neutron generation Preferably, at least 50% of the energy coming from the interacting protons is lost outside the target as compared to the energy deposited inside the target if this one would have a thickness where all the protons received from the proton beam release their thermal energy inside it.

In such embodiment, the aperture and thickness of the conical target are optimized so that the power density is preferably reduced to at least 50% as compared to the power density in a conical target with aperture and thickness where all the protons would release their thermal energy inside the target.

Additionally, the aperture and thickness of the conical target will be determined so that the number of generated neutrons in the target is at least 70% equal to the number of generated neutrons in a target where all the protons received from a proton beam would release their thermal energy inside the target.

Depending on (i) the shape of the conical target, (ii) the nature of the metal used for the target and (iii) the energy and intensity of the proton beam, the skilled person will be able to determine the above optimized ranges for thickness and aperture of the target, using any appropriate simulation software, and thereby reaching optimized yield for neutron activation using a compact neutron activator.

In a specific embodiment where the target has a right circular conical shape and is of Beryllium metal and the energy of the proton beam is between 65 and 75, for example 70 MeV, with an intensity between 0.30 and 0.40 mA, typically 0.35 mA, the thickness of the lateral walls is preferably between 4 and 4.6 min, for example 3.6 mm, the axial thickness 22.5 and 27.5 mm, typically 25 mm and the aperture of the conical target is preferably between 18 and 22°, for example 20°. The circular base of the target may be set between 27 and 33, for example 30 mm, in order to be adapted to typical beam-line size of 70 MeV cyclotrons.

Alternatively, in a second embodiment of the neutron activator, the aperture of the conical target and the thickness of its lateral walls are optimized so that
(i) the protons received from the proton beam lose all their energy within the metallic target, and
(ii) the stresses generated by the temperature gradients in the target remain within the elastic limit of the metallic target.

This embodiment may be appropriate when the proton beam characteristics (in terms of energy, intensity and width/current distribution) do not result in very high power densities in the solid target, as for example in the case of a 30 MeV-185 µA-30 mm beam on a water-cooled conical Beryllium or 30 MeV-140 µA-30 mm beam on a water-cooled conical Tantalum target.

In the latter embodiment, if a liquid such as water is used as a cooling fluid, it is indeed necessary to limit the thermal stress for avoiding the boiling of the cooling liquid and/or the deformation of the target.

The metallic target should be made of a material which thickness and composition allow an efficient neutron production, combined with good thermo-mechanical properties. Appropriate material includes without limitation Beryllium, Tantalum, Tungsten and its alloys (e.g. Tungsten-Rhenium or Tungsten-Copper).

Typically, the metallic target may be made of Beryllium.

In another specific embodiment, the metallic target is made of Tantalum. In such embodiment, the redox phenomenon typical of Tantalum at temperatures higher that 100° C. can be avoided by exposure of the inner surface of the lateral walls of the conical target to a vacuum atmosphere at a pressure of $10^{-3}$ mbar or Tower (small oxygen concentration), while the temperature of the outer surface in contact with water as cooling fluid is kept below 200° C. by the cooling effect of the water itself.

A preferred embodiment of the hollow conical target and its cooling system is illustrated in FIG. 2.

In such preferred embodiment, the cooling system comprises
a flow guide and
a cooling container.

In this preferred embodiment, the flow guide is in close proximity to the outer surface of the conical target and thereby delimits a cooling area for guiding the cooling fluid all along the outer surface of the conical target. The flow guide is connected to the cooling container which includes:
an inlet channel for conveying the cooling fluid to the flow guide and
an outlet channel for removing the cooling fluid from the flow guide.

More specifically, the flow guide is at least partly conical, preferably with similar shape to the conical shape of the target, so that said conical flow guide covers the outer surface of the conical target thereby delimiting a cooling area surrounding the outer surface of the target, sized in order to obtain along the target walls an optimized velocity distribution of the cooling liquid.

In a particular embodiment, there is no direct contact between the target and the flow guide so that the cooling fluid can contact all the outer surface of the target.

Advantageously, the assembly of the hollow conical target with the flow guide and the cooling container is cylinder-shaped so that it can be readily housed in the reflector-moderator surrounding said target assembly.

In a specific embodiment, thermocouples may be placed on or inserted at the outer surface of the target, for example at the base of the cone, for monitoring the thermal status of the target.

The Beryllium Reflector-Moderator

The neutron activator according to the present disclosure further includes a reflector-moderator which is peripheral to the neutron source and therefore, surrounds the target and its cooling system. The reflector-moderator further comprises the neutron activation area. Its function is to concentrate the activated neutrons in the area containing the activation samples (activation area) while efficiently slowing-down (moderating) the neutrons down to energies suitable for the activation of the selected isotopes.

The reflector-moderator is made of Beryllium or contains at least 90% of Beryllium metal. As shown in the example, the use of Beryllium as material for the reflector-moderator presents different advantages compared with other materials:
it presents a good capacity for containing the neutrons in some defined spectra, and thereby an improved activation efficiency in the activation area,
it is more adapted for activating the radioisotopes of interest, mainly Holmium particles.

The first reflector-moderator is hence configured to accommodate the neutron source and the material to be activated. The neutron activation area of the first reflector-moderator comprises a bore extending along a bore axis and configured to accommodate the neutron source so that the bore axis and the longitudinal axis are coaxial.

For example, in one specific embodiment of the neutron activator, the reflector-moderator surrounds a cylinder-shaped assembly of a hollow conical target and its cooling system (target assembly), said target assembly including
a right circular conical target,
a flow guide with similar conical shape to the target, and,
a cylinder-shaped cooling container as described in the previous sections.

In such specific embodiment, the reflector-moderator is cylindrical of circular cross-section, along the bore axis. Alternatively, the reflector-moderator may be cylindrical along the bore axis of any suitable other cross-section.

The dimensions of the reflector-moderator are set as to maximize the activation yield of the isotopes while keeping it as small as possible. Advantageously, the activator including the neutron source, the reflector-moderator, optionally together with the second reflector-moderator, has an overall dimension that does not exceed the volume of a cube of 1 meter side, preferably 0.75 meter side, and for example 0.50 meter side.

The reflector-moderator further includes activation channels for loading the material to be activated at the neutron activation area. The activation channels should enable the loading and unloading of the material to be activated. Said channels may be machined within the reflector-moderator. The skilled person will know how to determine the positions of said activation channels with respect to the target using appropriate simulations, in order to optimize the activation of the radioisotopes.

In a specific embodiment where the hollow conical target and its cooling system is cylinder-shaped (as described above), a plurality of activation channels may be disposed on concentric rings around the target.

More particularly, the activation area of the first reflector-moderator also comprises several activation channels extending along a channel axis parallel to the bore axis at the vicinity of the bore. In particular, the activation area comprises activation channels distributed around the bore. The activation channels are equally distributed around the bore. For example, in the represented embodiment, a first series of activation channels are evenly distributed around the bore at a first distance from the bore axis and a second series of activation channels are evenly distributed around the bore at a second distance from the bore axis, greater than the first distance.

Advantageously, the neutron activator further includes a remote material loading system, for allowing the remote loading-unloading of the material to be activated within the activation channels.

Although disclosed in relation with a target having a conical shape, the provisions as to the Beryllium reflector-moderator could be provided independently of the provisions regarding the shape of the target.

The Second Reflector-Moderator

The second reflector-moderator embedding the Beryllium reflector-moderator aims at further slowing down and scattering back the neutrons, already partially moderated, escaping the Beryllium reflector-moderator. Its main purpose is to optimize the activator performances while minimizing the volume, and therefore the cost, of the very expensive Beryllium reflector-moderator.

Preferably, the second reflector-moderator may be made of polyethylene, typically high-density polyethylene. The dimensions of the moderator will be such that the assembled activator, including the target, its cooling system, the reflector-moderator and the second reflector-moderator does not exceed a volume of a cube of 1 meter side, preferably 0.75 meter side, and for example 0.50 meter side.

Method for Neutron Activation

The activator according to the invention is dedicated to neutron activation of particles.

Therefore, another object of the present invention is to provide a method for neutron activation of a material, said method comprising:
a) providing the material to be activated,
b) placing the material at the activation area of a neutron activator as described in the present disclosure,
c) generating a proton beam at an energy suitable for neutron activation of said material, thereby activating said material.

In a specific embodiment, said material to be activated is contained within or in the form of a micro or nanoparticles, for example of Holmium-oxide micro or nanoparticles. Examples of Holmium-oxide particles are described in "New modality of curietherapy with holmium oxide submicronic particles." EANM 2009, Annual Congress of the European Association of Nuclear Medicine, Oct. 10-14, 2009, Barcelona, Spain Preferably, the microparticles or nanoparticles are in a liquid suspension.

For example, said material may be contained in a capsule, and said capsule is placed at the activation area by moving the capsule within the activation channels embedded in the reflector-moderator.

FIG. 3 represents an embodiment of a neutron activation system comprising:
a generator, such as a cyclotron 13, configured to produce a proton beam along a beam axis, the proton beam having an energy comprised between 16 MeV and 100 MeV, preferably 30 MeV and 70 MeV and a beam intensity up to 1 mA, preferably up to 350 µA for 70 MeV and up to 1 mA for 30 MeV,
a neutron activator arranged so that the longitudinal axis of the target is parallel, especially coaxial, to the beam axis, to produce neutrons from the interaction with the proton beam and to activate the material to be activated, and
a supplying device for loading one or more samples of material to be activated.

The method according to the invention is disclosed in relation with the neutron activation system of FIG. 3 which represents the different steps of the neutron activation.

Samples of material to be activated (activation samples) such as microparticles containing stable targeted isotopes are provided in the form of suitable capsules (15). The capsules are then loaded in the activation channels (5) through the supplying device which may include for example a shielded capsule loader (16) and a transfer system (14).

The supplying device is connected to the activation channels (5) and configured to move, preferably in an automated manner, samples of material to be activated along the activation channel (5). Advantageously, the method comprises the use of a pneumatic loading and unloading system, allowing the remote loading-unloading of the capsule(s) within the activation channels. For example, the capsules travel back and forth through a compressed air rabbit system allowing the remote loading/unloading of the particles suspension capsules. More advantageously, the pneumatic system allows also the cooling, by means of a flux of air flowing in all activation channels, of the heat generated by the interactions of the neutrons with the capsules and their content during the irradiation.

A proton beam (7) for example with energy between 16 and 100 MeV, preferably 30 and 70 MeV and intensities up to 1 mA, preferably up to 350 µA for 70 MeV and up to 1 mA for 30 MeV is then generated by a cyclotron (13).

The proton beam is directed to the metallic target (1) and the protons interact with the metallic target (for example made of Be), thereby generating fast (high energy) neutrons (12).

The target is cooled in the cooling area, using for example water flowing from an inlet channel to the outer surface of the target (2). In a specific embodiment, the target is cooled by a flow of cooling liquid, preferably water, at a static pressure comprised between 1 and 20 bar and reaching, near the target surface, speeds comprised between 8 and 24 m/s. The cooling aims at avoiding the boiling of the water while limiting erosion effects on the surface of the solid target or relevant vibration of the target structure. The cooling-water volume has the additional effect of giving a first moderation to the high-energy neutrons flowing out from the target. The relevance of this moderating effect depends on the thickness of the water layer. However in a specific embodiment of the activator design, the water-layer thickness is minimised at the advantage of keeping the activation samples as close as possible to the target and the beryllium reflector as compact as possible.

The neutrons are reflected and moderated in the first reflector-moderator (4) for reaching the activation area (10). Neutrons passing through the first reflector-moderator may be further moderated and scattered back by the second reflector-moderator (6).

The method for neutron activation according to the invention presents at least the following advantageous aspects:
- it is possible to activate the particles in injectable form, which is hardly achievable with a nuclear reactor,
- the use of a dedicated cyclotron-driven system allows a more flexible production and distribution of activated radioisotopes,
- no particles damage due to γ-heating (typical of nuclear reactors) occurs,
- short-life isotopes can be used and repeated treatment can be planned to increase the therapeutic efficiency,
- different types and sizes of nanoparticles can be used to tailor the therapy method to the specific case.

Use of the Neutron Activator

The present invention also relates to the use of the neutron activator as previously described, for producing radioisotopes, preferably for use in radiopharmaceuticals and medical devices.

The choice of the radioisotopes depends on three main characteristics: the half-life, the $\beta^-$ energy and the $\gamma$ energy (Table 1). Shorter half-life allows shorter permanence period in the treating unit (repeated treatment possible). Higher $\beta^-$ energy corresponds to higher therapeutic efficiency. Higher $\gamma$ energy corresponds to better detection with Single photon emission computed tomography (SPECT).

TABLE 1

| Radioisotope | Half-life | $\beta^-$ energy(keV) | $\gamma$ energy (keV) |
|---|---|---|---|
| Holmium 166 | 26.7 hours | 1840 | 80 |
| Lutetium 177 | 6.7 days | 497 | 208 |
| Rhenium 186 | 3.7 days | 1077 | 137 |
| Rhenium 188 | 17 hours | 2100 | 155 |
| Yttrium 90 | 2.7 days | 2080 | No |
| Gold 198 | 2.7 days | 1372.9 | 411.8 |
| Terbium 161 | 6.9 days | 157.4 | 74.5 |

In a specific embodiment, said radioisotope is a $\beta^-$ emitting radioisotope suitable for Nuclear Medicine applications, preferably $^{166}$Ho, $^{186}$Re, $^{188}$Re, $^{177}$Lu, $^{198}$Au, $^{90}$Y, $^{227}$Ra and $^{361}$Tb.

Holmium is of particular interest for the application of the present invention as it represents a very good compromise combining a short half-life and high $\beta^-$ energy, compared with the other radioisotopes.

Description of a Specific Embodiment of the Method and the Device According to the Invention The activator according to the Example, represented in FIG. 1, is a rectangular parallelepiped with a 50 cm width, 50 cm height, and 56 cm long. It is composed of:
- a hollow Beryllium conical target (1),
- a flow guide (2), an inlet channel (8) for conveying the cooling fluid to the flow guide (2) and an outlet channel (9) for removing the cooling fluid from the flow guide (2),
- a cylinder shaped cooling container (3) with an inlet and outlet channel,
- a Beryllium cylindrical reflector-moderator (4) with an internal diameter Di=100 mm, an external diameter De=160 mm and a length of 200 mm, hosting the activation channels (5) disposed coaxially around the target (1),
- a high density polyethylene second reflector-moderator (6).

The activation channels (5) are disposed on rings placed in a concentric way around the target. One ring of 16 channels allows a total loading capacity of 64 capsules/doses (4 per channel).

Table 2 presents the technical parameters of the activator.

TABLE 2

| PARAMETER | | VALUE | RATIONALE |
|---|---|---|---|
| Beam | Beam type | Protons | Best neutron yield |
| | Beam Energy | 70 MeV | Maximize neutron yield |
| | Beam current | 350 µA | Maximize neutron yield |
| | Beam current ref distrib. | Gaussian with FWHM = 1.4431 | Ref assumption for most challenging cooling conditions, real shape to be determined |
| | Collimators diameter | 30 mm | Minimize power density |
| Target | Material | Be | Maximize neutron yield, assure resistance minimize activation |
| | Shape | Hollow cone | Optimize heat exchange |
| | Overall dimensions | D = 35 mm H = 119.6 mm | Optimize heat exchange |
| Moderator-reflector | Material | Be/PEHD/Water | Optimize neutron fluxes and spectrum |
| | Shape | cylindrical | |
| | Be moderator-reflector dimensions | height = 20 cm diameter = 16 cm | |
| | PEHD cube dimensions | 0.5 × 0.5 × 0.6 m | |
| Activation channels | Dimensions | D = 11 mm | Minimize neutron leak |
| | Number | 16 | Maximize loading capacity |
| | Capsules per channel | 1 ÷ 4 | Maximize loading capacity |
| Activation capsules | Material | Peek/LDPE | |
| | Dimensions | Diameter 8.5 mm Length 45 mm | |

To limit erosion effects, the cooling water velocity has been limited at around 10 m/s, corresponding, with the present dimensions, to a flow rate of about 2 kg/s. With this condition, the maximum temperature of the wall at the interface target/water is expected around 150° C. To avoid boiling, the coolant (water) has to be pressurized at least at 5 bars.

Table 3 summarizes the cooling characteristics for the Be target.

TABLE 3

| Properties | Value |
|---|---|
| Target maximum temperature | 250° C. |
| Maximum temperature at the interface target/water | 50° C. |
| Maximum boundary heat flux | 8 MW/m$^2$ |

TABLE 3-continued

| Properties | Value |
|---|---|
| Minimum pressure needed in the cooling system | 5 bar |
| Mass flow rate | 2 kg/s |

In order to choose the best material for the reflector-moderator placed around the target and hosting the activation channels, a set of Monte Carlo calculations was done by comparing the following materials: water, polyethylene, beryllium, graphite and lead.

Figure 4:
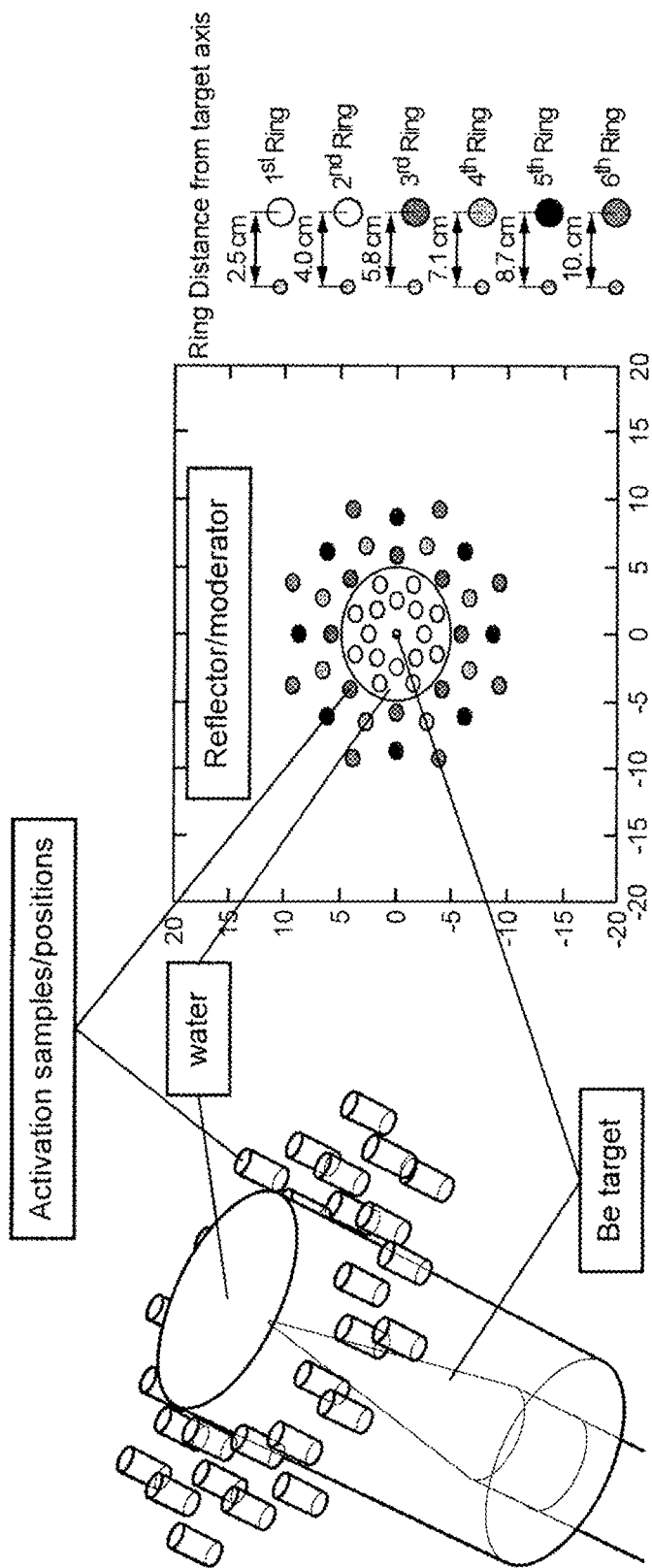
FIG. 4 is an illustration of the activation samples positions with respect to the hollow conical target

Given the cross-section for the $^{165}$Ho(n,γ)$^{166}$Ho transmutation (reported in FIG. 4 together with the one for the $^{176}$Lu(n,γ)$^{177}$Lu), most favorable neutron energies are in the thermal (0-10$^{-7}$ MeV) and epithermal (10$^{-7}$÷5×10$^{-3}$ MeV) range.

Figure 5:
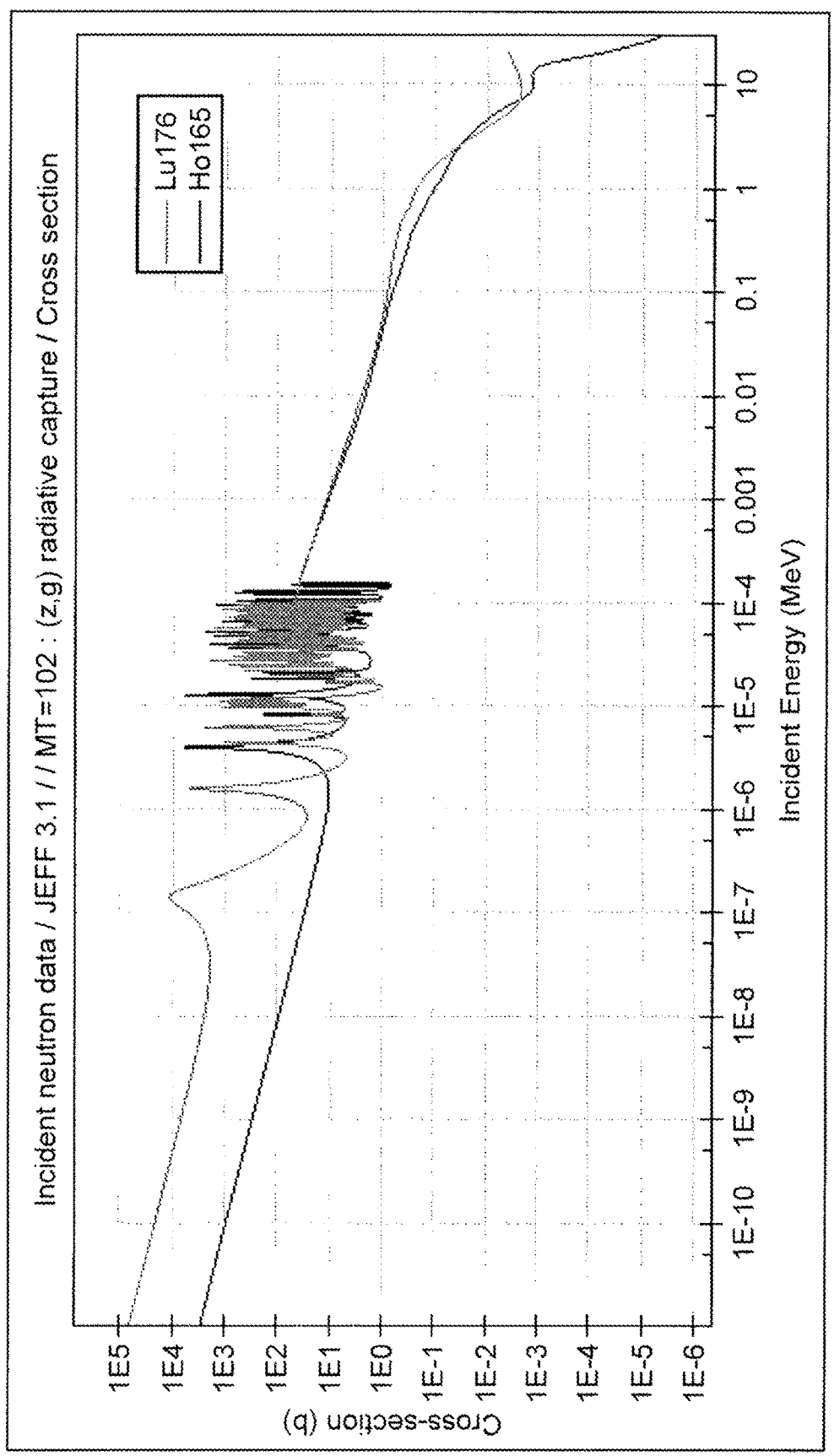
FIG. 5 is a graph presenting the cross-sections for the $^{165}$Ho(n,γ)$^{166}$Ho and the $^{176}$Lu(n,γ)$^{177}$Lu transmutations.
Figure 6:
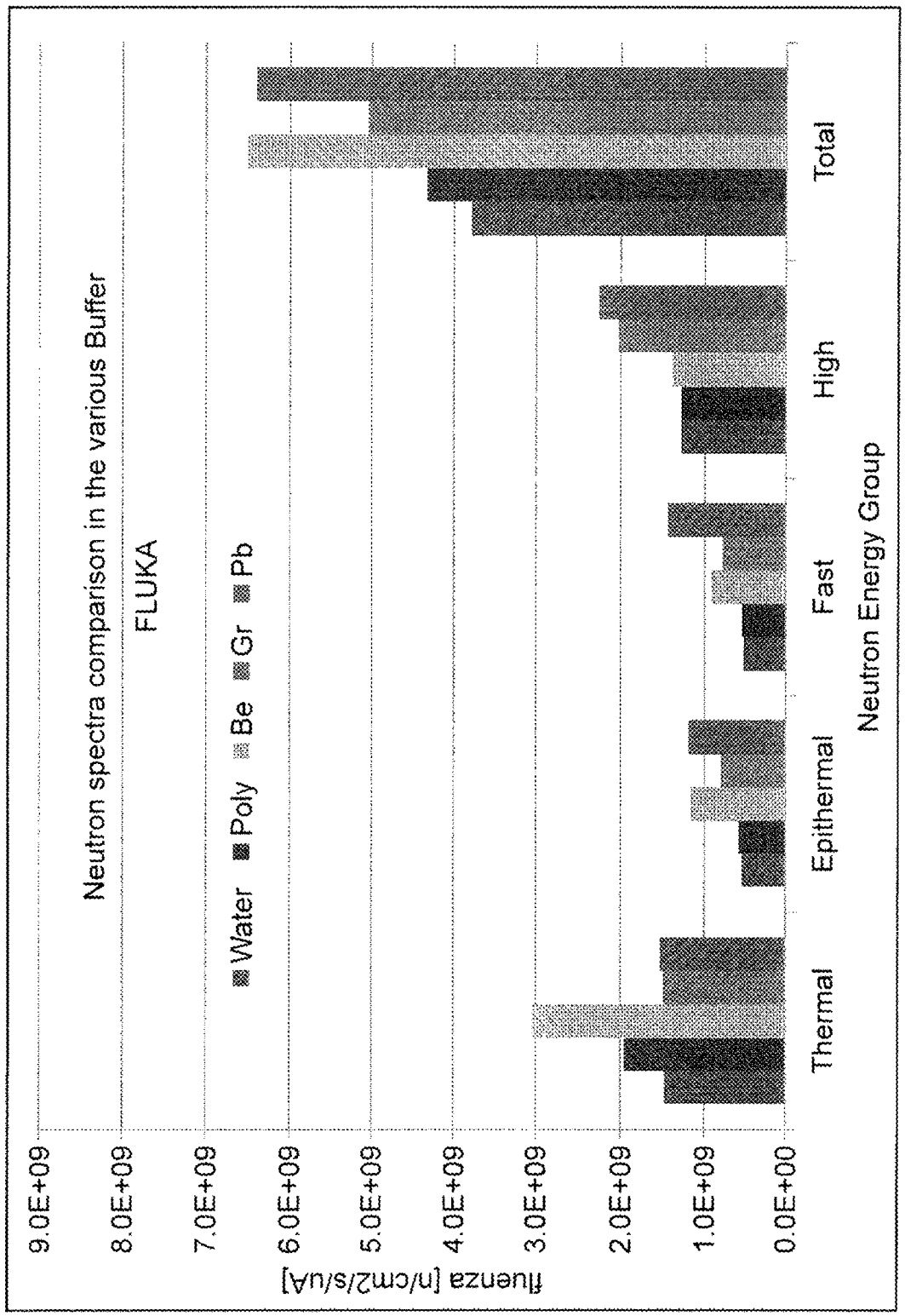
FIG. 6 is a graph presenting the neutron spectra with various moderators.

As shown in the graph of FIG. 5 representing the neutron spectra in activation channel as shown in FIG. 4, the resulting neutron spectrum is most favorable in the case of the Beryllium, which shows

- as can be seen by comparing the total neutron fluxes for Be and Pb, the higher neutron absorption of the Be is compensated by a better neutron-confinement, resulting in a total neutron flux comparable to Pb,
- furthermore, Be shows very good moderation, yielding significantly higher fluxes in the thermal region with respect to all the other materials, and same level as Pb in the epithermal region.

As a result presented in table 4, the $^{166}$Ho activation yield is significantly better with the Be reflector-moderator.

TABLE 4

| Reflector-moderator | Saturation Activity (Bq/g/uA) |
|---|---|
| Water | 3.88E+08 |
| Polyethylene | 4.27E+08 |
| Beryllium | 9.19E+08 |
| Graphite | 4.33E+08 |
| Lead | 6.56E+08 |

With this activator according to the Example replacing the hollow Beryllium conical target by a hollow Tantalum conical target, the $^{166}$Ho activation yield is much higher with the Be reflector-moderator as presented in table 5.

TABLE 5

| Reflector-moderator | Saturation Activity (Bq/g/uA) |
|---|---|
| Beryllium | 2.1E+09 |

The invention claimed is:

1. A neutron activator for neutron activation of a material, the neutron activator being configured to produce neutrons from an interaction with a proton beam emitted along a beam axis, the proton beam having an energy comprised between 16 MeV and 100 MeV and a beam intensity up to 1 mA, the neutron activator comprising:
   a neutron source comprising a metallic target presenting a longitudinal axis, and
   a Beryllium reflector-moderator peripheral to the neutron source and comprising a neutron activation area configured to accommodate the neutron source and the material, the neutron activation area of the Beryllium reflector-moderator comprising a bore extending along a bore axis and configured to accommodate the neutron source so that the bore axis and the longitudinal axis are coaxial aligned,
   wherein the neutron activation area of the Beryllium reflector-moderator further includes at least one activation channel machined in the Beryllium reflector-moderator and extending along a channel axis parallel to the bore axis at the vicinity of the bore, the at least one activation channel being configured to be loaded with the material.

2. The neutron activator according to claim 1, wherein the neutron activation area comprises a plurality of activation channels distributed around the bore.

3. The neutron activator of claim 1, wherein the metallic target has a hollow conical shape, and further comprising a cooling area in direct contact with the outer surface of the target for receiving a flow of fluid for cooling the target during neutron generation.

4. The neutron activator according to claim 3, further comprising, housed in the Beryllium reflector-moderator:
   an inlet channel conveying the cooling fluid,
   a flow guide delimiting the cooling area for guiding the cooling fluid along the outer surface of the target as a flow from the inlet channel,
   an outlet channel for removing the cooling fluid from the flow guide.

5. The neutron activator according to claim 4, wherein the flow guide is at least partly conical so that said conical flow guide covers the outer surface of the conical target thereby delimiting the cooling area surrounding the outer surface of the conical target.

6. The neutron activator according to claim 3, wherein an aperture of the conical target forms an angle comprised between 20° and 45°.

7. The neutron activator according to claim 1, wherein the metallic target is made of Beryllium or Tantalum.

8. The neutron activator according to claim 1, wherein said Beryllium reflector-moderator is cylindrical along the bore axis.

9. The neutron activator according to claim 1, wherein dimensions of the neutron activator do not exceed a volume of a cube of 1 meter side.

10. The neutron activator according to claim 9, wherein the dimensions do not exceed the volume of a cube of 0.75 meter side.

11. The neutron activator according to claim 9, wherein the dimensions do not exceed the volume of a cube of 0.50 meter side.

12. The neutron activator according to claim 2, wherein the activation channels are equally distributed around the bore.

13. A neutron activation system for neutron activation of a material, comprising:
   a generator configured to produce a proton beam along a beam axis, the proton beam having an energy comprised between 16 MeV and 100 MeV, and a beam intensity up to 1 mA,
   a neutron activator according to claim 1 arranged so that the longitudinal axis of the target is parallel to the beam axis.

14. The neutron activation system according to claim 13, wherein the generator is configured to produce the proton beam having an energy comprised between 30 MeV and 70 MeV.

15. The neutron activation system according to claim 13, wherein the generator is configured to produce the proton beam having a beam intensity up to 350 μA for 70 MeV.

16. The neutron activation system according to claim 13, wherein the generator is configured to produce the proton beam having a beam intensity up to 1 mA for 30 MeV.

17. A neutron activation system for neutron activation of a material, comprising:
- a generator configured to produce a proton beam along a beam axis, the proton beam having an energy comprised between 16 MeV and 100 MeV, and a beam intensity up to 1 mA,
- a neutron activator according to claim 1 arranged so that the longitudinal axis of the target is parallel to the beam axis,
- the neutron activation system further comprising a supplying device for loading the material, the supplying device being connected to said at least one activation channel and configured to move samples of material along the at least one activation channel.

18. A method for neutron activation of a material, said method comprising:
a) providing the material,
b) placing the material at the activation area of the neutron activator as defined in claim 1,
c) generating a proton beam at an energy comprised between 16 MeV and 100 MeV and having an intensity up to 1 mA.

19. The method of claim 18, wherein the target is cooled by a flow of cooling liquid at a static pressure comprised between 1 and 20 bar and reaching velocity comprised between 8 m/s and 24 m/s at the target surface.

20. The method of claim 18, wherein said material is in the form of a microparticle or nanoparticle.

21. The method of claim 19, wherein the cooling liquid is water.

22. The method of claim 18, wherein the proton beam has an energy between 16 MeV and 100 MeV.

23. The method of claim 18, wherein the proton beam has an energy between 30 MeV and 70 MeV.

24. The method of claim 18, wherein the proton beam has an intensity up to 350 µA for 70 MeV.

25. The method of claim 18, wherein the proton beam has an intensity up to 1 mA for 30 MeV.

26. The method of claim 20, wherein said material is in the form of Holmium-oxide microparticles or nanoparticles.

* * * * *